United States Patent [19]

Buntin et al.

[11] Patent Number: 4,759,923

[45] Date of Patent: Jul. 26, 1988

[54] PROCESS FOR LOWERING SERUM CHOLESTEROL USING POLY(DIALLYLMETHYLAMINE) DERIVATIVES

[75] Inventors: George A. Buntin; Bernard J. Scheve, both of Wilmington, Del.

[73] Assignee: Hercules Incorporated, Wilmington, Del.

[21] Appl. No.: 66,678

[22] Filed: Jun. 25, 1987

[51] Int. Cl.⁴ .............................................. A61K 31/14
[52] U.S. Cl. ...................................... 424/440; 424/439; 424/464; 514/183; 514/359; 514/408; 514/556; 514/642; 514/740; 514/743; 514/760; 514/782; 514/824; 514/937; 514/951; 514/963; 514/964; 522/151
[58] Field of Search ........................... 424/25, 32, 34; 514/183, 359, 408, 556, 642, 740, 743, 760, 782, 824, 937, 951, 963, 964

[56] References Cited

U.S. PATENT DOCUMENTS

| | | |
|---|---|---|
| 3,383,281 | 5/1968 | Wolf et al. .......................... 167/65 |
| 3,692,895 | 9/1972 | Nelson et al. ......................... 424/78 |
| 3,700,623 | 10/1972 | Keim ................................. 260/80.3 |
| 3,980,770 | 9/1976 | Ingelman et al. ...................... 424/79 |
| 4,016,262 | 4/1977 | Fauland et al. ....................... 514/46 |
| 4,041,153 | 8/1977 | Howard .............................. 424/151 |
| 4,210,671 | 7/1980 | Murai et al. ......................... 514/623 |
| 4,343,811 | 8/1982 | Hurnaus et al. ...................... 514/415 |
| 4,432,968 | 2/1984 | Page et al. ............................ 424/81 |

OTHER PUBLICATIONS

Kuron et al., "The Bile Acid Binding the Hypocholesterolemic Action of Two Water-Soluble Polymers", International Journal for Research and Investigation on Atherosclerosis and Related Diseases, pp. 353-360, Nov. 1980, vol. 37.

Primary Examiner—John Kight
Assistant Examiner—S. A. Acquah
Attorney, Agent, or Firm—Marion C. Staves

[57] ABSTRACT

It has been found that certain derivatives of poly(diallylmethylamine) are therapeutically effective serum cholesterol lowering agents.

24 Claims, No Drawings

PROCESS FOR LOWERING SERUM CHOLESTEROL USING POLY(DIALLYLMETHYLAMINE) DERIVATIVES

STATEMENT OF THE INVENTION

This invention relates to a process for the reduction of serum cholesterol in animals including humans. More particularly the invention relates to a process of orally administering therapeutically effective amounts of certain derivatives of poly(diallylmethylamine) to an animal in need of such treatment.

BACKGROUND

The liver is the primary source of cholesterol produced in humans. Bile acid salts are major end-products of cholesterol catabolism, which aid in fat digestion. A 4-6 gram bile salt pool is maintained in the body and about 5% of this bile acid pool is normally excreted daily.

Bile acid salt sequestrants increase the rate of bile acid salt excretion and since the bile acid salts inhibit the conversion of cholesterol to bile acid salts, their removal increases the rate of hepatic metabolism of cholesterol. In addition, however, a compensatory increase in the rate of hepatic biosynthesis of cholesterol occurs to maintain hepatic cholesterol balance and more importantly a resultant lowering of serum and arterial cholesterol and thus lowering of low density liporotein is observed. The exact mechanism for this lowering is not known.

The bile acid sequestrants cholestyramine (Cuemid ®, Questran ®), colestipol (Colestid ®), and DEAE-Sephadex (Secholex ®, Polidexide ®) are currently available. The disadvantages of cholestyramine are its amine-like odor and unpleasant mouth feel. The mouth feel is characterized by a gritty, sand-like feel. Although colestipol is odorless, the intrinsic mouth-feel characteristics of this resin are similar to those of cholestyramine. Also, large doses (8-16 gr. per day) of cholestyramine are required to reduce serum cholesterol, which causes constipation in some people.

Certain water soluble, non-cross-linked cationic polymers are known bile acid salt sequestrants and serum cholesterol lowering agents, e.g., ionenes of the formula:

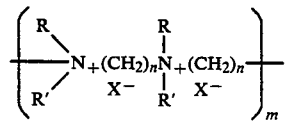

as claimed in U.S. Pat. No. 4,027,009 and disclosed in "Atheriosclerosis", 37, 353-360 (1980). The latter reference discloses another water soluble, non-cross-linked polymer, the quaternary amine poly(diallyldimethylammonium chloride),

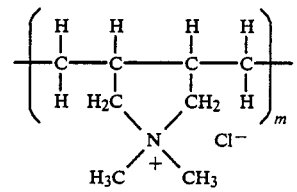

as a cholesterol lowering agent. These polymers when tested in dogs are effective in lowering cholesterol, but are non-cross-linked and toxic.

An objective of tnis invention is to develop cholesterol lowering agents without unpleasant mouth-feel characteristics.

Another objective of this invention is to develop cholesterol lowering agents that can be administered in a pill or capsule form or incorporated in food or candy.

SUMMARY OF THE INVENTION

It has now been discovered that derivatives of poly(diallylmethylamine) are superior to the cholestyramine of the prior art in cholesterol lowering and bile acid binding power. The derivatives of poly(diallylmethylamine) are polymeric resins prepared from poly(diallylmethylamine) having a molecular weight between 1000 and 100,000 (number average molecular weight) modified by quaternizing and optionally crosslinking. Other cholesterol lowering resins are also claimed using poly(diallylmethylamine) and attaching hydrophobic side chains to the amine groups, or attaching bile acid like side chains to the amine groups of the hydrochloride and methylammonium chloride salts of poly(diallylmethylamine).

Since the five resin classes of this invention have superior cholesterol lowering power over cholestyramine, a therapeutic dosage amount that is lower than that required for cholestyramine is now possible. This lower dosage amount permits the use of unit dosage forms, such as capsules, that eliminate the unpleasant mouth-feel characteristics associated with cholestyramine use.

Accordingly, this invention involves oral administration of compounds useful for lowering the blood serum cholesterol of an animal in need thereof, comprising a resin selected from the group consisting of:

(A) A quaternized poly(diallylmethylamine) cross-linked through about 0.03% to about 50% of its nitrogen radicals by heating at a temperature of at least about 200° C. for a period of time sufficient to cross-link to the percentage desired;

(B) Poly(diallylmethylamine) cross-linked through about 0.03% to about 50% of its nitrogen radicals by heating at a temperature below about 200° C. in the presence of a multifunctional cross-linking agent and quaternized with a quaternizing agent before, during or after cross-linking;

(C) A quaternized poly(diallylmethylamine) cross-linked through radiation by electron or gamma rays at a dose of about 2 to about 30 megarads;

(D) Poly(diallylmethylamine) quaternized through about 1% to about 10% of its nitrogen radicals with hydrophobic saturated alkyl halide radicals having from about 6 to about 22 carbon atoms; and (E) Poly(diallylmethylamine) quaternized through about 1% to about 10% of its nitrogen radicals with a hydroxy substituted radical selected from the group consisting of derivatives of cholanic acid, derivatives of ergosterol, and derivatives of phenanthrene.

DESCRIPTION OF THE PREFERRED EMBODIMENTS

The preparation of poly(diallylmethylamine hydrochloride),

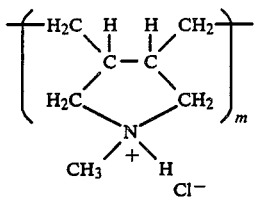

is well documented in the literature [Negi, Y. et al, J. of Polymer Science (Part A-1) 5, 1951–65 (1967); Butler, G.B. et al JACS 79, 3128, 3131 (1957) and JACS 80, 3615–3618 (1958)].

Poly(diallylmethylamine hydrochloride) may be completely neutralized with base to give poly(diallylmethylamine), the formula of which is

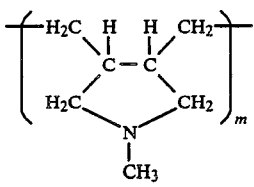

In embodiment (A) the nitrogen radicals of poly(diallylmethylamine) are quaternized to the extent of about 50% to about 97% of the nitrogen present and then the quaternized compound is heated at a temperature of at least 200° C. for a period of time sufficient to cross-link the quaternized poly(diallylmethylamine) through about 0.03% to about 50% of its unquaternized nitrogen radicals. Typical quaternizing agents that can be used to quaternize poly(diallylmethylamine) in accordance with this invention are hydrochloric acid, 1-chloro-2,3-dihydroxy-propane, or a haloglycerol derivative. The period of time the quaternized poly(diallylmethylamine) is heated will vary from about one-half hour to about 50 hours or more depending on the percentage of cross-linking desired and the specific quaternized poly(diallylmethylamine) being cross-linked.

In embodiment,(B) poly(diallylmethylamine) is cross-linked through about 0.03% to about 50% of its nitrogen radicals with a multifunctional cross-linking agent. Typical multifunctional cross-linking agents that can be used in accordance with this invention are dihaloalkanes such as 1,3-dichloropropane, 1,3-dibromopropane, and 1-bromo-3-chloropropane; halooxiranes such as epichlorohydrin; dihaloalkenes such as 1,4-dichloro-2-butene, or dihaloarylalkyls. The amount of cross-linking agent used will vary from about 3.0% to about 50% based on the weight of the poly(diallylmethylamine) used. The cross-linking will be carried out at a temperature below 200° C., most preferably from about 60° C. to about 150° C., for a period of time sufficient to obtain the desired percentage of crosslinking. In general, the time period will vary from about one-half hour to about 20 or more hours. In addition to being cross-linked with a multifunctional cross-linking agent the remaining free nitrogen radicals of the poly(diallylmethylamine) shall be quaternized with quaternizing agents as described in embodiment (A). The quaternizing in embodiment (B) can be performed before, during or after the cross-linking process.

In embodiment (C) the nitrogen radicals of poly(diallylmethylamine) are quaternized to the extent of about 1% to about 100% of the nitrogen present with a quaternizing agent as described in embodiment (A) and then the quaternized poly(diallylmethylamine) is cross-linked by radiation using electron or gamma rays at a dose of about 2 to about 30 megarads.

In embodiment (D) of this invention poly(diallylmethylamine) is modified by attaching hydrophobic side chains to about 1% to about 10% of its nitrogen radicals. The polyto(diallymethylamine) is modified by reacting with an alkylbromide or alkylchloride having between about 6 and about 22 carbon atoms, such as cetyl bromide, chlorooctane, stearyl bromide and the like. Amounts of alkylbromide or chloride used in accordance with embodiment (D) will vary from about 1.0% to about 10% based on the weight of the poly(diallylmethylamine) being modified.

In embodiment (E) poly(diallylmethylamine) is modified by attaching radicals of derivatives of cholanic acid, phenanthrene, or ergosterol through about 1% to about 10% of its nitrogen radicals. Typical of the derivatives to be used in embodiment (E) are:
muricholic acid
homocholic acid
dihomocholic acid
haemulcholic acid
3β, 7β, 12α-trihydroxy -5β-cholanoic acid
Cholestra 5-8(14)-diene -Δ$^{7,α}$,-succinic acid, 3β-hydroxy
ursocholic acid
3-β-cholic acid
5α-cholic acid
α-muricholic acid
β-muricholic acid
Cholan-24-oic acid, 3, 7, 21-trihydroxy,-(3α, 5β, 7α)
24-norcholane-19, 21, 23-trioic acid, 3, 5, 14 trihydroxy-3β, 5β, 14β(would lead to crosslinked material or material having residual chloro groups)
5β-cholan-24-oic acid 3α, 12α, 16α-trihydroxy-
hyocholic acid
cholalin
5α-cholan-24-oic acid, 3β, 7α, 12α-trihydroxy-
3β, 5α, 6β-trihydroxycholanic acid
5β-cholan-24-oic acid, 3α, 4α, 12α-trihydroxy-
5β-cholan-24-oic acid, 3α, 6α, 12α-trihydroxy-
2, 3 secours-12-ene-2, 3, 28-trioic acid
5β-cholan-24-oic acid, 3α, 12α, 15α-trihydroxy-
5α-cholan-24-oic acid, 3α, 6α, 7α-trihydroxy-
24-norcholan-23-oic acid 3, 12, 17 trihydroxy,-(3β, 5β, 12α)
Cholan-24-oic acid, 3, 7, 12-trihydroxy-, (3α, 7α, 12α)
5α-cholan-24-oic acid, 3α, 6β, 7αtrihydroxy-
choleinic acid
estra-1, 3, 5(10)-triene-6-acetic acid, 3, 16, 17-trihydroxy-, (6β, 16α, 17β)
estra-1, 3, 5(10)-triene-6-butanoic acid, 3, 16, 17-trihydroxy-, (7α, 16α, 17β)
cholan-24-oic acid, 3, 5, 12-trihydroxy-, (3α, 5β, 12α)
2,3,-secolean-12-ene, 2, 3, 28-trioic acid, (14β)
1-phenantheneacetic acid, 2 carboxytetradecahydro-7-hydroxy-2,4b-dimethyl-, [1S-(1α, 2β, 4aβ, 4bα, 7β, 8aβ, 10aα)]

24-norchol-3-ene 4, 23-dicarboxylic acid 12-hydroxy-, (5β, 12α)

cholane-24-carboxylic acid, 3, 7, 12, 23 tetrahydroxy-, (3α, 5β, 7α, 23R)

cholan-24-carboxylic acid, 3, 7, 12, 23-tetrahydroxy-, (3α, 5β, 7α, 23S)

cholan-24-oic acid, 3, 6, 7, 12-tetrahydroxy- 1-phenanthraneacetic acid, 2-carboxy -1,2,3,4,4a,4b,5,6,7,8, 10, 10a-dodecahydro-7-hydroxy -2, 4b-dimethyl-, [1S-(1α, 2β, 4aβ, 4bα, 7α,10aα)]

cholan-24-oic acid, 3, 12, dihydroxy -6-(1-hydroxy-1-methylethyl)-, (3α, 5α, 6α, 12α)

pregnane-21-carboxylic acid 3, 6, 17-trihydroxy-, (3α, 5β, 6α, 17α)

3,4-Secolupane-3, 28-dioic acid, 23-hydroxy-,(4S)

24-nor-3,4-secolupane-3, 28-dioic acid, 4-hydroxy-,(4S)

cholan-24-oic acid, 3, 12-dihydroxy-16-(1-hydroxycyclohexyl)-, (3α, 5β, 12α, 16β)

In embodiments (D) and (E), the resins become insoluble when they complex with bile acids.

As stated in the summary, this invention involves oral administration of cholesterol lowering polymeric resins. The resins can be orally administered to living animals, e.g., humans, by any suitable means, and in any suitable form. For example, the resins can be incorporated into ordinary foodstuffs and beverages in an amount sufficient to produce the desired effect. Also, the resins can be incorporated into pharmaceutical compositions customarily employed for oral administration.

Pharmaceutical compositions containing the resin can be in liquid form, for example, a solution (in the case of embodiments (D) and (E) only) or suspension, specifically adapted for oral administration or in solid form, for example, a tablet, capsule, pill or packaged powder. These compositions can be prepared using pharmaceutically acceptable carriers or diluents, such as, for example, starch, glucose, lactose, gelatin, sucrose, etc., and the like. Sustained release forms of administration are also acceptable.

The amount administered will, of course, vary depending among other things, on the size of the animal subject, the particular animal to be treated, and the general health of the animal. Human dosage can be determined with regard to established medical practice. In general, however, about 250 mg to about 7500 mg, most preferably about 500 mg to about 4000 mg will be administered in unit doses 2 to 4 times daily.

While the agents of this invention are excellent bile acid sequestrants and very effective in lowering serum cholesterol, it may be desirable in certain instances to decrease serum cholesterol levels below that which can be achieved with the sequestering agents of this invention alone. In those cases, the cholesterol lowering agents of this invention can be used in combination with known drugs which reduce serum cholesterol by mechanisms other than sequestration. Examples of such known drugs which can be used in combination with the cholesterol lowering agents of this invention are Clofibrate (the ethylester of p-chlorophenoxyisobutyric acid); nicotinic acid and its derivatives, such as Acifran ®, Probucol (which is 2,2,-di(t-butyl-phenol-4-thio-)propane); Neomycin; P-aminosalicylic acid; Mevinolin: and tne like. The methods for using such known drugs in combination with the cholesterol lowering agents of this invention, such as methods of combining the drugs, methods of administration, dosages and the like will be obvious to those skilled in the art.

The following examples illustrate various embodiments of the claimed invention without limiting its scope.

Example 1 illustrates embodiment (A) of this invention, while Examples 2-13 illustrate embodiment (B).

EXAMPLE 1

14 parts of poly(diallylmethylamine) quaternized with hydrochloric acid to the extent of about 90% of the nitrogen present (finely ground) are placed in a tube immersed in diisopropylbenzene at 203° C. for 48 hours. 13.3 parts of this heated material is washed three times with water. The washed solid is finally dried at 60° C. under vacuum leaving 5.4 parts of black granular solid. It analyzes for 8.92% nitrogen. The resulting product is useful in lowering cholesterol in animals.

EXAMPLE 2

To 12 parts of poly(diallylmethylamine) in 162 parts of methanol are added 1.6 parts of 1,3-dichloropropane multifunctional cross-linking agent and 8.9 parts of 1-chloro-2,3-dihydroxypropane quaternizing agent. The solution is stirred at reflux for 16 hours. It is stripped of solvent on a rotary evaporator at 40° C.-20 mm and then at 30° C.-1 mm. 19.6 parts of a brittle, orange, resinous solid are produced. Aqueous extraction indicates it is 83.3% water insoluble.

EXAMPLE 3

To 12 parts of poly(diallylmethylamine) in 162 parts of methanol are added 0.3 parts of epichlorohydrin multifunctional cross-linking agent and the solution is stirred at reflux. After about 0.5 hr. a gel forms. It is heated at reflux for an additional 0.5 hours, then 11 parts of 1-chloro-2,3-dihydroxypropane quaternizing agent in 81 parts of methanol are added. The gel is stirred at reflux for 15 hours. It is then stripped of methanol on a rotary evaporator at 40° C. -20 mm and finally at 30° C.-1 mm, producing 24 parts of orange-yellow, resinous solid. The solid is 6.5% nitrogen (K.jd), 14.2% chlorine, and 12.0% ionic chlorine, and is 90.0% insoluble in water.

EXAMPLE 4

To 12 parts of poly(diallylmethylamine) in 162 parts of methanol are added 1.6 parts of 1,3-dichloropropane multifunctional cross-linking agent. The solution is stirred at reflux for 16 hours. Then to the solution which has become more viscous are added 8.9 parts of 1-chloro-2,3-dihydroxypropane quaternizing agent and reflux continued with stirring for 16 hours additional. The solution is then stripped of solvent on a rotary evaporator at 60° C. -20 mm and then at 60° C. -1 mm, producing 22.0 parts of orange-red resinous solid. It is analyzed 6.7% N, 14.1% Cl, and 11.6% ionic Cl. It is 83.3% water insoluble.

EXAMPLE 5

To 12 parts of poly(diallylmethylamine) in 162 parts of methanol are added 1.05 parts of 1-bromo-3-chloropropane multifunctional cross-linking agent and 10.35 parts of 1-chloro-2,3-dihydroxypropane quaternizing agent. The solution is stirred at reflux for 16 hours. The solution is then evaporated on a rotary evaporator at 60° C.-20 mm and the residue dried at 60° C.-1 mm, producing 23.3 parts of yellow-orange resinous powder. It is 96.7% insoluble in water.

EXAMPLES 6 THROUGH 13

Following the procedure of Example 5, various amounts of 1-bromo-3-chloropropane multifunctional cross-linking agent are added to give products with different amounts of cross-linking. These are:

| Example | 1-bromo-3-chloropropane Parts | (Percent)* | Product Parts | % Water Insoluble |
|---|---|---|---|---|
| 6 | 2.1 | 17.50 | 23.0 | 100 |
| 7 | 1.05 | 8.75 | 22.7 | 96 |
| 8 | 0.703 | 5.86 | 22.8 | 86 |
| 9 | 0.503 | 4.37 | 22.6 | 80 |
| 10 | 0.42 | 3.50 | 22.1 | 80 |
| 11 | 0.30 | 2.50 | 22.1 | 80 |
| 12 | 0.15 | 1.25 | 21.3 | 70 |
| 13 | 0 | 0.0 | 12.0 | 0.0 |

*Based on 12 parts of poly(diallylmethylamine)

In vivo tests were conducted using cross-linked and quaternized poly(diallymethylamine) resins similar to those obtained from Examples 2–13. Before in vivo testing, each of these resins is washed with water to remove soluble materials. Each is then mixed with 1220 parts distilled water, stirred slowly for 15 minutes, the swollen gel particles allowed to settle, and the clear superatant water decanted. Fresh distilled water is added and the operation repeated, and yet again for a total of three washes. The swollen particulate solid product is then filtered on paper at 20 mm, sucked dry, and placed in a tray to air dry for three days. It is then dried at 60° C. -1 mm to a constant weight.

The resins were tested using Japanese quail. Cholestyramine and colestipol were included in the test for comparison. The results of these tests are summarized in Tables 1 and 2.

An artherogenic diet comprising a basal diet listed in Table 5, and 0.5% cholesterol was fed to the quail during the tests. The diet is taken from Morrissey, et al., "Cholestyramine in Japanese Quail", *Artery*, Vol. 5, p. 182 (1979). For feeding and testing the quail, the procedure used is taken from Day, et al., "Utility of a Selected Line of Japanese Quail For the Discovery of New Anti-Artheriosclerosis Drugs", *Laboratory Animal Science*, Vol. 27, p. 817 (1977). To summarize the procedure, the resins were fed to different quail groups at 0.25% of the artherogenic diet for 2 weeks. Cholestyramine and colestipol were also fed at 0.5% and 1.0% of the diet. The quail were fed continually during this period. After 14 days, the blood serum cholesterol in mg./100 ml serum was determined for each group of birds.

The data from Table 1 show that the resins are superior to cholestyramine and colestipol in reducing serum cholesterol.

The data from Tables 2A and B show the effect of various amounts of cross-linking agent (1-bromo-2-chloropropane as used in Examples 6–13) on cholesterol lowering. Table 2A records the amount of agent used, body weights of the subject birds, food intake, and resin intake. Table 2B records the serum cholesterol of the subject birds and the cholesterol lowering.

TABLE 1

| Resin Treatment | Crosslinking Agent | Resin Intake Day 7 | Resin Intake Day 14 | Number of Quail | Serum Cholesterol (mg/100 ml) Day 0 | Serum Cholesterol (mg/100 ml) Day 7 | Serum Cholesterol (mg/100 ml) Day 14 | Cholesterol Lowering (%) |
|---|---|---|---|---|---|---|---|---|
| STUDY NO. 1 | | | | | | | | |
| 0.25% Cholestyramine | — | 321 | 265 | 5 | 189 | 605 | 514 | 32 |
| 0.5% Cholestyramine | — | 677 | 557 | 6 | 189 | 347 | 348 | 54 |
| 1.0% Cholestyramine | — | 1428 | 1206 | 5 | 191 | 256 | 267 | 65 |
| 0.25% Colestipol | — | 305 | 266 | 6 | 192 | 776 | 656 | 13 |
| 0.5% Colestipol | — | 621 | 543 | 6 | 193 | 513 | 446 | 41 |
| 1.0% Colestipol | — | 124 | 106 | 6 | 192 | 285 | 280 | 63 |
| 0.25% Example 3 | E | 274 | 247 | 6 | 193 | 445 | 469 | 38 |
| 0.25% Example 4 | D | 325 | 280 | 6 | 192 | 469 | 447 | 41 |
| 0.25% Example 5 | B | 327 | | 6 | 193 | 478 | 412 | 46 |
| Untreated Controls | — | | 285 | 6 | 192 | 925 | 756 | — |
| STUDY NO. 2 | | | | | | | | |
| Untreated Controls | — | — | — | 5 | 216 | 455 | 651 | — |
| Example 2 | D | 266 | 277 | 5 | 214 | 324 | 355 | 45 |
| Example 2 | D | 282 | 252 | 5 | 215 | 343 | 393 | 40 |
| Cholestyramine (Questran) (.25%) | — | 305 | 269 | 5 | 216 | 239 | 797 | — |
| Cholestyramine (Questran) (.5%) | — | 518 | 527 | 5 | 216 | 485 | 283 | 57 |

Cross-linking Agents: E = Epichlorhydrin, D = 1,3-dichloropropane, B = 1-bromo-3-chloropropane

TABLE 2A

| Resin Treatment[a] | 1-Bromo-3-Chloro-Propane (%) | Body Wts. (g) Day 1 | Body Wts. (g) Day 14 | Food Intake (g/bird/day) | Resin Intake (mg/kg/day) |
|---|---|---|---|---|---|
| Control | — | 109 | 109 | 12.2 | — |
| Example 6 | 17.50 | 114 | 114 | 13.0 | 288 |
| Example 7 | 8.75 | 115 | 115 | 13.2 | 288 |
| Example 8 | 5.86 | 116 | 115 | 13.3 | 288 |
| Example 9 | 4.37 | 107 | 108 | 12.3 | 284 |
| Example 10 | 3.50 | 113 | 114 | 12.8 | 280 |
| Example 11 | 2.50 | 111 | 110 | 11.0 | 249 |
| Example 12 | 1.25 | 113 | 113 | 10.9 | 241 |
| Example 13 | 0.00 | 114 | 114 | 12.5 | 272 |

TABLE 2B

| Resin Treatment[a] | Serum Cholesterol (mg/100 ml) Day 0 | Day 7 | Day 14 | Day 14 Cholesterol Lowering (%) |
|---|---|---|---|---|
| Control | 209 | 820 | 873 | — |
| Example 6 | 213 | 410 | 499 | 43 |
| Example 7 | 201 | 492 | 524 | 40 |
| Example 8 | 198 | 432 | 442 | 49 |
| Example 9 | 212 | 499 | 529 | 39 |
| Example 10 | 188 | 642 | 638 | 27 |
| Example 11 | 201 | 547 | 630 | 28 |
| Example 12 | 176 | 452 | 602 | 31 |

TABLE 2B-continued

| Resin Treatment[a] | Serum Cholesterol (mg/100 ml) | | | Day 14 Cholesterol Lowering (%) |
|---|---|---|---|---|
| | Day 0 | Day 7 | Day 14 | |
| Example 13 | 193 | 500 | 654 | 25 |

Example 14 illustrates the use of the compound of Example 1 in a foodstuff.

EXAMPLE 14

Two cups of flour, one teaspoon of salt, one-half teaspoon of baking soda, and 170 g of the compound of Example 1 are mixed in a bowl. One fourth cup of butter cut in small pieces is added along with one-half cup of milk, one teaspoon of vinegar and one egg. The batter is mixed until a stiff dough is obtained. The dough is kneaded thoroughly and rolled until very thin so that a cracker weight about 3 to about 5 grams is obtained. The formed cracker is baked at 400° F. in an oven for ten minutes or until lightly brown. The cooked crackers are sprinkled with salt and each contains about one gram of cholesterol lowering drug. Several of the crackers are ground up into fine particles and fed to quail as in Examples 6 through 13 at a dose of about 300 mg/kg/day. The quails show a cholesterol lowering of about 40 percent compared to controls receiving a diet where no cracker is present.

Example 15 illustrates embodiment (C) of this invention.

EXAMPLE 15

1-chloro-2,3-dihydroxy-propane (0.45 moles) is reacted with poly(diallylmethylamine) hydrochloride (0.85 moles) in 350 parts of water by the slow addition of 0.03 moles of sodium hydroxide at room temperature. The solution is acidified at room temperature and the solution stripped under vacuum. The resulting solids are dried overnight in a vaccum oven. The solids are then irradiated under a nitrogen atmosphere at a dose of 20 megarads with a High Voltage Engineering 2.5 Mev Van de Graff generator to cross-link the sample. The resulting product is useful in lowering cholesterol in animals.

Examples 16–24 illustrates embodiment (D) of this invention.

EXAMPLES 16–24

100 parts of poly(diallylmethylamine hydrochloride) are added to a 50% solution of sodium hydroxide until basic, to make poly(diallylmethylamine). The water solution is decanted from the precipitate. The taffy-like material is washed two times with distilled water and squeezed as dry as possible between paper towels. 150 ml of anhydrous ethyl alcohol is added, and the mixture is stirred and heated to reflux or until the solids dissolve. The appropriate amount of alkyl halide is added (Tables 3 and 4) and stirred at reflux for 20 hours. The reaction is cooled and enough hydrochloric acid is added until the solution pH is at 5-6. The ethanol is removed by vacuum. The dry polymer is extracted twice with heptane, and 0.5 parts of solid are collected from the heptane extract. The dried polymer is collected. Resin Examples 16–20 as listed in Table 3 and Examples 21–24 in Table 4 are prepared by this method. Examples 18–20 are for comparison.

For in vivo testing of samples from Examples 16–24, the same diet and testing procedures used to test the resins from Examples 2–13 are used. The basal diet fed quail during testing is listed in Table 5. The atherogenic diet is the basal diet plus 0.5% added cholesterol. The sample resins are tested at 0.25% of the diet.

Tables 3 and 4 show cholesterol lowering results of poly(diallylmethylamine) modified by attaching various hydrophobic groups, i.e., cetyl, octyl, and stearyl, compared with cholestyramine. The cholesterol lowering studies indicate that small amounts of hydrophobic side chain substitution does produce serum cholesterol lowering greater than cholestyramine. The effects on serum cholesterol of 1% and 10% cetylbromide modified poly(diallylmethylamine) are superior to cholestyramine.

TABLE 3

| Example No. | Side Group | Resin Intake | | Serum Cholesterol (mg/100 ml) | | | % Lowering of Cholesterol |
|---|---|---|---|---|---|---|---|
| | | 7 day | 14 day | Day 0 | Day 7 | Day 14 | |
| None (Control) | — | — | — | 235 | 965 | 1599 | — |
| Cholestyramine (Control) | — | 312 | 330 | 235 | 764 | 959 | 40 |
| 16 | 1% Cetyl bromide | 335 | 375 | 235 | 469 | 531 | 67 |
| 17 | 10% Cetyl bromide | 300 | 323 | 235 | 560 | 769 | 52 |
| 18 | 100% Cetyl bromide | 344 | 334 | 236 | 844 | 1010 | 37 |
| 19 | 50% Cetyl bromide | 354 | 347 | 234 | 912 | 1121 | 30 |
| 20 | 100% Stearyl bromide | 322 | 319 | 234 | 943 | 1228 | 23 |

TABLE 4

| Example No. | Side Group | Day 14 Serum Cholesterol | % Cholesterol Lowering |
|---|---|---|---|
| None (Control) | | 948 | — |
| Cholestyramine (.25%) (Control) | | 732 | 23 |
| 21 | 1% Chlorooctane | 543 | 43 |
| 22 | 0.5% Cetyl Bromide | 515 | 46 |
| 23 | 1.0% Cetyl Bromide | 488 | 49 |
| 24 | 2.0% Cetyl Bromide | 655 | 31 |

TABLE 5

| Basal Diet | | |
|---|---|---|
| Ingredient | % of diet | kg |
| Glucose | 40.0 | 24.0 |
| Corn oil | 2.0 | 1.2 |
| Lard | 8.0 | 4.8 |
| Soybean meal (44% prot) | 34.0 | 20.4 |
| CaHPO$_4$ (Anhydrous) | 2.83 | 1.7 |
| Ground Limestone | 5.0 | 3.0 |

TABLE 5-continued

| Ingredient | Basal Diet % of diet | kg |
|---|---|---|
| Iodized salt | 0.43 | 0.26 |
| Cellulose (Avicel) | −6.7 | 4.06 |
| DL-methionine | 0.4 | 0.24 |
| Trace mineral mix | 0.11 | 0.065 |
| Vitamin mix | 0.5 | 0.30 |
| BHT | 0.03 | 0.018 |
| Total | — | 60.043 |

Example 25 illustrates the use of the compounds in Example 16 in candy.

EXAMPLE 25

Two cups of sugar, one cup of maple syrup, and one-half teaspoons of salt, one and one-half cups of water, and 115 g of the cholesterol lowering drug of one percent cetylbromide modified poly(diallylmethylamine), Example 16, are combined in a pan. This is heated slowly until the sugar and cholesterol lowering drug dissolve. This is cooked at 260° F. until a hard ball is obtained (about 15 minutes). The pan is removed from the heat and two tablespoons of butter and one quarter teaspoon of peppermint are stirred into the ball. The ball is cooled and pulled until it became difficult to pull. This is then cut into pieces weighing about five grams and each piece contains about one gram of the chloesterol lowering drug. Several of the large pieces of the candy are cut into very small pieces (ground in a cyrogenic mill) and fed to quail at a dose of about 300 mg/kg/day. After two weeks the quail show a cholesterol lowering of about 35 percent compared to quail receiving a diet containing no candy.

Examples 26 and 27 illustrate embodiment (E) of this invention.

EXAMPLE 26

To make a poly(diallylmethylamine) modified with a chlorinated radical of a cholanic acid derivative, the following procedural steps are followed. The tetrahydropyran derivative of cholanyl chloride is prepared as follows in steps 1–4:

(1) 50 parts of cholic acid are added to 162 parts methanol, and then 2 drops of sulfuric acid are added. This solution is refluxed for two days, cooled and filtered;

(2) the resulting product of step (1) is added to 297.8 parts chloroform and 3 equivalents of dihydropyran plus a drop, 0.05 parts, of hydrochloric acid, stirred at room temperature for two days and evaporated;

(3) the resulting product of step (2) is added to 736 parts of dry ether in a 3 neck flask fitted with a condensor and a stirrer. Seven (7) parts of lithium aluminum hydride are added in 15 portions over ½ hour. After 1 hour, 7 parts of water are added dropwise over a 30 minute period. Seven (7) parts 15% sodium hydroxide are added followed by 21 parts water. This solution is filtered, dried over potassium carbonate, filtered, and evaporated;

(4) to 30 parts of the product from step 3 in 200 cc chloroform and 9.9 parts of pyridine is added 5.5 parts of thionyl chloride dropwise. This is refluxed 30 minutes, cooled, and water added. The layers are separated and the chloroform layer dried over potassium carbonate, filtered and dried. The poly(diallylmethylamine) modified product is prepared in step 5;

(5) Nine parts of the tetrahydropyran derivative of cholanyl chloride prepared as above are added to a solution of 15 parts of poly(diallylmethylamine) in ethanol (60 parts) and the mixture refluxed overnight. The solvent is stripped in vacuum, and the resulting solids washed with hexane to remove any excess tetrahydropyran derivative of cholanyl chloride. The resulting solids are then dissolved in 60 parts of ethanol/water, 50/50, and acidified with aqueous hydrochloric acid and refluxed for one hour to remove the tetrahydropyran groups. The solvent is stripped and the product dried overnight.

EXAMPLE 27

To make a hydrochloride salt of poly(diallylmethylamine) modified with a chlorinated radical of a cholanic acid derivative, the following procedural steps are followed:

(1) step (1) of Example 26 is repeated;

(2) 8 parts of the product of step (1) are dissolved in 297.8 parts of chloroform to which are added 2 equivalents of dihydropyran and 3 drops of hydrochloric acid. This solution is stirred for 2 days and evaporated;

(3) to the product of step (2), 223.4 parts of chloroform and 3 equivalents of pyridine are added, and then one equivalent of thionyl chloride is added dropwise. This is refluxed for 0.5 hours, cooled, and water added. The chloroform layer is dried over potassium carbonate, filtered and evaporated;

(4) Three and one-half parts of the 3,7, or 12 chloromethylcholate as prepared above is added to a solution of 13 parts of poly(diallylmethylamine) in 70 parts of ethanol. The solution is refluxed overnight. The solvent is stripped under vacuum and the resulting solids washed with hexane to remove any unreacted chloromethylcholate. The resulting solids are dissolved in a solution of ethanol/water, 50/50, and acidified with aqueous hydrochloric acid to remove the tetrahydropyran groups and hydrolyze the methyl ester. The solvent is stripped and the product dried overnight.

Example 28 is a comparator where poly(diallylmethylamine) is 100% modified with cholanyl chloride.

EXAMPLE 28

Three parts of the tetrahydropyran derivative of cholanyl chloride as prepared in Example 26 is added to an ethanol (20 parts) solution of poly(diallylmethylamine) (0.5 parts) and refluxed overnight. The solvent is stripped under vacuum, and the resulting solids washed with hexane and dried. These solids are then dissolved in a solution of (20 parts) of ethanol/water 50/50, acidified with aqueous hydrochloric acid and refluxed for one hour to remove the tetrahydropyran groups. The solvent is stripped, and the product dried in an oven overnight.

The products from Examples 26–28 are tested to determine their "in vitro" binding capacity. The procedure used is that of Mosbach, *Arch. Biochem.*, 51, p 402 (1954).

The UV procedure used to follow "in vitro" binding is given below.

1. Weigh 20 mg resin into 13×100 mm glass screw-capped test tubes.

2. Add 5 ml of taurocholate solution prepared by dissolving 1.565 g sodium taurocholate in 100 mil distilled water (146μmoles/5 ml).

3. Mix the resin and bile salt solution with sufficient agitation to keep the resin particles suspended for 1 hour at ambient temperature. 4. Allow the resin to settle and transfer 10 μl of clear supernatant fluid to a 13×100 mm screwcapped test tube. A 10 μl aliquot of the bile salt solution (Step #2) is transferred to a second tube.

5. Add 5 ml 65% H₂SO₄ to each tube and heat in water bath at 60° C. for 15 minutes.

6. Allow tubes to cool and determine absorbance at 320 nm.

7. Calculate μ moles TCA bound to resin by the equation $$\mu\text{moles } TCA \text{ bound} = \frac{O.D. \ TCA \text{ soln.} - O.D. \text{ of Unbound } TCA \text{ in Resin Tube}}{O.D. \text{ of } TCA \text{ soln.}}$$

The results are tabulated in Table 6.

TABLE 6

| Example | Sequestering Agent | Taurocholate* bound μm per gram Sequestrant | | |
|---|---|---|---|---|
| | | Water | 0.15 M NaCl | 0.3 M NaCl |
| Control | cholestyramine | 83 | 68 | 58 |
| 26 | PDAMA**-cholylchloride (10%) | 95 | 87 | 89 |
| 27 | PDAMA**-3,7 or 12-chlorocholate (5%) | 105 | 87 | 88 |
| 28 | PDAMA**-cholylchloride (100%) | 53 | N.A. | N.A. |

*a bile acid
**poly(diallylmethylamine)

The data from Table 6 show that poly (diallylmethylamine) modified with chlorocholic acid derivatives are superior bile acid sequestrants to cholestyramine.

In Examples 29 and 30, the LD₅₀ of a cross-linked water insoluble (Example 29) and an uncross-linked water soluble (Example 30) product are illustrated.

EXAMPLE 29

Epichlorohydrin (0.45 mole) is added to a water solution (350 parts water) of poly(diallylmethylamine) hydrochloride (0.85 mole) and 0.03 mole of a 4% sodium hydroxide solution is added. The solution is heated at 45°-50° C. for about two and one-half hours whereupon it gells. The reaction is heated for another four and one-half hours. The solid product is dried in a vacuum at 105° C. for thirty hours. The dried product is ground and placed in an extraction thimble and extracted with water for about 55 hours. The resulting solid is dried in a vacuum oven at 105° C. for 16 hours and submitted for LD₅₀ studies in mice. The LD₅₀ is found to be greater than 5 g/kg.

EXAMPLE 30

To 20 g of poly(diallylmethylamine) is added 0.6 g of cetyl bromide. This is refluxed in ethanol for twenty hours. A solid is obtained by evaporation of the solvent and the resulting solid is washed with hexane to remove residual cetyl bromide. The solid is dried at 100° C. under vacuum. The LD₅₀ of this material is found to be 2.42 g/kg.

What we claim and desire to protect by Letters Patent is:

1. A method for lowering the blood serum cholesterol of an animal in need thereof comprising orally administering to the animal a therapeutically effective amount of a pharmaceutical compound selected from the group consisting of:

(A) A quaternized poly(diallylmethylamine) cross-linked through about 0.03% to about 50% of its nitrogen radicals by heating at a temperature of at least about 200° C. for a period of time sufficient to cross-link to the percentage desired;

(B) Poly(diallylmethylamine) cross-linked through about 0.03% to about 50% of its nitrogen radicals by heating at a temperature below about 200° C. in the presence of a multifunctional cross-linking agent and quaternized with a quaternizing agent before, during or after cross-linking;

(C) A quaternized poly(diallylmethylamine) cross-linked through radiation by electron or gamma rays at a dose of about 2 to about 30 megarads;

(D) Poly(diallylmethylamine) quaternized through about 1% to about 10% of its nitrogen radicals with hydrophobic saturated alkyl halide radicals having from about 6 to about 22 carbon atoms; and (E) Poly(diallylmethylamine) quaternized through about 1% to about 10% of its nitrogen radicals with a hydroxy substituted radical selected from the group consisting of derivatives of cholanic acid, derivatives of ergosterol, and derivatives of phenanthrene.

2. The method of claim 1 wherein the pharmaceutical compound is a quaternized poly-(diallylmethylamine) cross-linked through about 0.03% to about 50% of its nitrogen radicals by heating at a temperature of at least about 200° C. for a period of time sufficient to cross-link to the percentage desired.

3. The method of claim 1 wherein the pharmaceutical compound is poly(diallylmethylamine) cross-linked through about 0.03% to about 50% of its nitrogen radicals by heating at a temperature below about 200° C. in the presence of a multifunctional cross-linking agent and quaternized with a quaternizing agent before, during or after cross-linking.

4. The method of claim 1 wherein the pharmaceutical compound is a quaternized poly(diallylmethylamine) cross-linked through radiation by electron or gamma rays at a dose of about 2 to about 30 megarads.

5. The method of claim 1 wherein the pharmaceutical compound is poly(diallylmethylamine) quaternized through about 1% to about 10% of its nitrogen radicals with hydrophobic saturated alkyl halide radicals having from about 6 to about 22 carbon atoms.

6. The method of claim 1 wherein the pharmaceutical compound is poly(diallylmethylamine) quaternized through about 1% to about 10% of its nitrogen radicals with a hydroxy substituted radical selected from the group consisting of derivatives of cholanic acid, derivatives of ergosterol, and derivatives of phenanthrene.

7. The method of claim 1 wherein the pharmaceutical compound is administered incorporated in a foodstuff.

8. The method of claim 7 wherein the foodstuff is a cracker.

9. The method of claim 1 wherein the foodstuff is candy.

10. The method of claim 1 wherein the pharmaceutical compound is administered as a tablet.

11. The method of claim 1 wherein the pharmaceutical compound is administered in a solution.

12. The method of claim 1 wherein the pharmaceutical compound is administered as a suspension in a pharmaceutically acceptable carrier.

13. The method of claim 1 wherein the pharmaceutical compound is administered in combination with at least one drug which reduces serum cholesterol by a mechanism other than sequestration.

14. The method of claim 3 wherein the multifunctional cross-linking agent is 1-bromo-3-chloropropane.

15. The method of claim 5 wherein the hydrophobic saturated alkyl halide is cetyl bromide.

16. The method of claim 6 wherein the hydroxy substituted radical is a derivative of cholanic acid.

17. The method of claim 13 wherein the drug is a derivative of nicotinic acid.

18. A pharmaceutical composition for lowering blood serum cholesterol comprising in unit dosage form from about 250 mg to about 7500 mg of a nontoxic pharmaceutical compound selected from the group consisting of:

(A) A quaternized poly(diallylmethylamine) cross-linked through about 0.03% to about 50% of its nitrogen radicals by heating at a temperature of at least about 200° C. for a period of time sufficient to cross-link to the percentage desired;

(B) Poly(diallylmethylamine) cross-linked through about 0.03% to about 50% of its nitrogen radicals by heating at a temperature below about 200° C. in the presence of a multifunctional cross-linking agent and quaternized with a quaternizing agent before, during or after cross-linking;

(C) A quaternized poly(diallylmethylamine) cross-linked through radiation by electron or gamma rays at a dose of about 2 to about 30 megarads;

(D) Poly(diallylmethylamine) quaternized through about 1% to about 10% of its nitrogen radicals with hydrophobic saturated alkyl halide radicals having from about 6 to about 22 carbon atoms; and (E) Poly(diallylmethylamine) quaternized through about 1% to about 10% of its nitrogen radicals with a hydroxy substituted radical selected from the group consisting of derivatives of cholanic acid, derivatives of ergosterol, and derivatives of phenanthrene.

19. The pnarmaceutical composition of claim 18 wherein the pharmaceutical compound is a quaternized poly(diallylmethylamine) cross-linked through about 0.03% to about 50% of its nitrogen radicals by heating at a temperature of at least about 200° C. for a period of time sufficient to cross-link to the percentage desired.

20. The pharmaceutical composition of claim 18 wherein the pharmaceutical compound is poly(diallylmethylamine) cross-linked through about 0.03% to about 50% of its nitrogen radicals by heating at a temperature below about 200° C. in the presence of a multifunctional cross-linking agent and quaternized with a quaternizing agent before, during or after cross-linking.

21. The pharmaceutical composition of claim 18 wherein the pharmaceutical compound is a quaternized poly(diallylmethylamine) cross-linked through radiation by electron or gamma rays at a dose of about 2 to about 30 megarads.

22. The pharmaceutical composition of claim 18 wherein the pharmaceutical compound is poly(diallylmethylamine) quaternized through about 1% to about 10% of its nitrogen radicals with hydrophobic saturated alkyl halide radicals having from about 6 to about 22 carbon atoms.

23. The pharmaceutical composition of claim 18 wherein the pharmaceutical compound is poly(diallylmethylamine) quaternized through about 1% to about 10% of its nitrogen radicals with a hydroxy substituted radical selected from the group consisting of derivatives of cholanic acid, derivatives of ergosterol, and derivatives of phenanthrene.

24. The pharmaceutical composition of claim 18 wherein the pharmaceutical compound is combined with at least one drug which reduces serum cholesterol by a mechanism other than sequestration.

* * * * *

UNITED STATES PATENT AND TRADEMARK OFFICE
CERTIFICATE OF CORRECTION

PATENT NO. : 4,759,923
DATED : July 26, 1988
INVENTOR(S) : George A. Buntin and Bernard J. Scheve It is certified that error appears in the above-identified patent and that said Letters Patent is hereby corrected as shown below:

Column 3, line 51 " tnrough "

should read -- through --

Column 4, line 16 " polyto(diallymethylamine) "

should read -- poly(diallylmethylamine) --

Column 5, line 21 " tnis "

should read -- this --

Column 5, line 64 " tne "

should read -- the --

Column 16, line 9 " pnarmaceutical "

should read -- pharmaceutical --

UNITED STATES PATENT AND TRADEMARK OFFICE
CERTIFICATE OF CORRECTION

PATENT NO. : 4,759,923
DATED : July 26, 1988
INVENTOR(S) : George A. Buntin and Bernard J. Scheve It is certified that error appears in the above-identified patent and that said Letters Patent is hereby corrected as shown below:

Column 11, lines 29 and 30 " chloesterol "

should read -- cholesterol --

Signed and Sealed this

Twentieth Day of December, 1988

*Attest:*

DONALD J. QUIGG

*Attesting Officer*   *Commissioner of Patents and Trademarks*